US012782370B2

(12) United States Patent
Patzke

(10) Patent No.: US 12,782,370 B2
(45) Date of Patent: Nov. 3, 2026

(54) GLOBAL TEST FOR DETERMINING THE STATUS OF THE BLOOD COAGULATION SYSTEM

(71) Applicant: Siemens Healthcare Diagnostics Products GmbH, Marburg (DE)

(72) Inventor: Juergen Patzke, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 708 days.

(21) Appl. No.: 18/177,466

(22) Filed: Mar. 2, 2023

(65) Prior Publication Data

US 2023/0280359 A1 Sep. 7, 2023

(30) Foreign Application Priority Data

Mar. 3, 2022 (EP) .................................... 22159912

(51) Int. Cl.

| | |
|---|---|
| ***G01N 33/86*** | (2006.01) |
| ***C12Q 1/56*** | (2006.01) |
| ***G01N 21/76*** | (2006.01) |
| ***G01N 21/82*** | (2006.01) |
| ***G01N 33/573*** | (2006.01) |
| ***G01N 33/577*** | (2006.01) |
| ***G01N 33/68*** | (2006.01) |

(52) U.S. Cl.
CPC .................................. *G01N 33/86* (2013.01)

(58) Field of Classification Search
None
See application file for complete search history.

(56) References Cited

U.S. PATENT DOCUMENTS

| | | | |
|---|---|---|---|
| 3,996,345 A | 12/1976 | Ullman et al. | |
| 5,830,681 A | 11/1998 | Hursting et al. | |
| 2003/0219845 A1 | 11/2003 | Ruiz et al. | |
| 2010/0280412 A1 | 11/2010 | Hellstern et al. | |
| 2019/0127442 A1 * | 5/2019 | Ruggeri ................ | C12N 9/644 |

FOREIGN PATENT DOCUMENTS

| | | |
|---|---|---|
| CN | 108697763 A | 10/2018 |
| EP | 0303983 A2 | 2/1989 |
| EP | 0515194 A2 | 11/1992 |
| EP | 0420332 B1 | 4/1995 |
| EP | 0456152 B1 | 11/1998 |
| EP | 0802986 B1 | 9/2001 |
| EP | 1541676 A1 | 6/2005 |
| EP | 1544621 A1 | 6/2005 |

(Continued)

OTHER PUBLICATIONS

Matthew D. Rand, Jennifer B. Lock, Cornells van't Veer, Donald P. Gaffney, Kenneth G. Mann, Blood Clotting in Minimally Altered Whole Blood, Blood, vol. 88, Issue 9, (Year: 1996).*

(Continued)

*Primary Examiner* — Brittany I Fisher
(74) *Attorney, Agent, or Firm* — Harness Dickey & Pierce P.L.C.

(57) ABSTRACT

Embodiments of the present invention are in the field of blood coagulation diagnostics and relate to a test for establishing an individual's blood coagulation system status based on the amount of in-vitro-generated F1+2 peptide, and to a test kit for use in such a method.

16 Claims, 9 Drawing Sheets

(56) References Cited

FOREIGN PATENT DOCUMENTS

| | | | |
|---|---|---|---|
| EP | 2168985 | A1 | 3/2010 |
| EP | 2177625 | A1 | 4/2010 |
| JP | S6470498 | A | 3/1989 |
| JP | 2008137988 | A | 6/2008 |
| JP | 2019501911 | A | 1/2019 |
| WO | WO 9506877 | A1 | 3/1995 |

OTHER PUBLICATIONS

Siemens Healthineers, Enzygnost F1+2 (monoclonal), 2021 (Year: 2021).*

Udenfriend, S. et al., Scintillation proximity radioimmunoassay utilizing 125-I-labelled ligands, Proc. Natl. Acad. Sci. USA 1985, 82, 8672-8676; 1985.

Capecchi, Marco et al., "Relationship between thrombin generation parameters and prothrombin fragment 1+2 plasma levels", International Journal of Laboratory Hematology 2021, vol. 43, p. 248-251; 2021.

Kapoor, Sargam et al., The Role of Neutrophils in Thrombosis, Thromb Res. 2018, 170, p. 87-96.

Kintigh, Jeremy et al., "A review of commercially available thrombin generation assays", Research and Practice in thrombosis and hemostasis 2018, No. 2, p. 42-48.

Litvinov, Rustem I. and Weisel, John W., Role of red blood cells in haemostasis and thrombosis, ISBT Sci Ser. 2017, 12 (1), p. 176-183.

Newman, D.J. et al., Particle enhanced light scattering immunoassay. Ann Clin Biochem 1992; 29: 22-42.

Peula, J.M. et al., Covalent coupling of antibodies to aldehyde groups on polymer carriers. Journal of Materials Science: Materials in Medicine 1995; 6: 779-785.; 1995.

Hemker, H.C. et al., Continuous Registration of Thrombin Generation in Plasma, its use for the Determination of the Thrombin Potential, Thrombosis and Haemostasis 1993, Bd. 70(4), p. 617-624.

Duarte, Rita C.F et al., "Thrombin generation assays for global evaluation of the hemostatic system: perspectives and limiations", Revista Brasileira de Hematologia e Hemoterapia 2017, vol. 39(3), p. 259-265; 2017.

Alamin, Amin A., The Role of Red Blood Cells in Hemostasis, Sermin Thromb Hemost 2021, 47, p. 26-31.

Kappel, Andreas et al., "Coagulation assays based on the Luminescent Oxygen Channeling Immunoassay technology", Clin Chem Lab Med 2011, vol. 49(5), p. 855-860.

Office Action from Japanese Application No. 2023-031529 dated Aug. 18, 2026.

* cited by examiner

GLOBAL TEST FOR DETERMINING THE STATUS OF THE BLOOD COAGULATION SYSTEM

CROSS-REFERENCE TO RELATED APPLICATION(S)

The present application claims priority under 35 U.S.C. § 119 to European Patent Application No. 22159912.9, filed Mar. 3, 2022, the entire contents of which are incorporated herein by reference.

FIELD

One or more example embodiments of the present invention are in the field of blood coagulation diagnostics and relate to a novel global test for establishing an individual's blood coagulation system status based on the amount of in-vitro-generated F1+2 peptide, and to a test kit for use in such a method.

BACKGROUND

Blood coagulation (hemostasis) is regulated through the interplay of various activators, inhibitors, and positive and negative feedback mechanisms. Defects in this framework can lead to an imbalance in the blood coagulation system and result either in a hemorrhage or a thrombosis.

Thrombin, a serine protease, is the central enzyme of plasmatic blood coagulation, the main function of which is the induction of fibrin polymerization and hence clot formation. When the need arises, the formation of thrombin is set in train through the activation of the enzymatically inactive precursor molecule prothrombin. In order to limit the coagulation process locally and restrict its duration when an injury occurs, coagulation is promptly curtailed inter alia by free thrombin being complexed by inhibitory factors such as antithrombin or a2-macroglobulin (a2M) and thus inactivated. Disturbances in the processes that regulate thrombin formation or inhibition can lead to hypercoagulatory or hypocoagulatory states and thus to pathological disturbances in coagulation. Detecting the formation and inhibition of thrombin is therefore immensely valuable in providing information about the coagulation status of a particular individual.

The ability (potential) that is inherent (endogenous) in a sample—in the case of plasma samples the ability that is inherent in the plasma—for the formation and inhibition of enzymatically active, free thrombin is also referred to as the endogenous thrombin potential (ETP). Since the individual thrombin potential of a sample is determined by all biological components that are present in a material under investigation and that are able to influence the formation and inhibition of thrombin, the ETP determination is suitable for use both as a global test that can be used for determining multiple components of the hemostasis system and for monitoring treatment measures.

One parameter, the determination of which is the preferred mechanism of quantifying the endogenous thrombin potential, is the time/concentration integral or area under the thrombin formation curve [see EP 420332-B1, EP 802986-B1 and Hemker et al. (1993) Thromb. Haemostasis 70: 617-624]. This parameter is a measure of the amount and activity of the endogenous thrombin that has been present since time t=0 in a sample of coagulating plasma.

To determine the ETP, the reaction kinetics of a thrombin substrate are measured in a sample of coagulation-capable plasma via the release of a measurable indicator. Since the thrombin substrate concentration is set such that the substrate cannot be used up completely in the course of the reaction, the amount of indicator released is ideally proportional to the enzymatic activity of the thrombin that is formed in the course of the coagulation reaction.

The various commercially available test systems that permit automated performance of the ETP determination are extremely complex, because the complicated process of thrombin activation and inhibition and the determination of thrombin activity over time requires a large number of highly specific customizations, for example the selection of suitable thrombin substrates, the provision of specific calibrators, the addition of fibrin inhibitors, and the use of test-specific algorithms for evaluating the measured values (see for example Kintigh et al. (2018) A review of commercially available thrombin generation assays. Res Pract Thromb Haemost. 2:42-48). A further disadvantage of the known test systems for determining the ETP is that in practice it has not up to now been possible to perform automated determination of the ETP in whole blood. The known commercial test systems are suitable only for determination of the ETP in platelet-poor (PPP) or platelet-rich (PRP) plasma, the use of fluorogenic measurement methods being a prerequisite when using PRP.

SUMMARY

An object underlying one or more example embodiments of the present invention is thus that of providing a test method that is the equal of the ETP test method in the information it provides on the functionality of the blood coagulation cascade or status of the blood coagulation system of an individual, but that permits a simplified test setup, a simplified test evaluation, and in particular also the execution of the test in PRP and whole blood as the sample matrix.

It has been found that the quantitative determination of the amount of F1+2 that is formed in vitro in a sample of whole blood or plasma of an individual (also referred to as "a subject") ensures the establishment of an individual's blood coagulation system status and advantageously permits a simplified test setup, a simplified test evaluation, and in particular also the execution of the test in PRP and whole blood as the sample matrix.

The present invention thus provides a method for establishing an individual's blood coagulation system status, wherein the method—like the prior art method for determining the ETP—comprises the following steps that result in the activation of the blood coagulation system in vitro:

a. providing a reaction mixture by adding a coagulation activator to a sample from the individual and
b. incubating the reaction mixture.

The method according to an embodiment of the present invention has the characteristic feature compared to the prior art that the method additionally comprises the following steps:

c. quantitative determination of the amount of F1+2 in the reaction mixture and
d. establishing the blood coagulation system status by comparing the amount of F1+2 thus measured in the reaction mixture with a reference value or reference value range that represents the normal blood coagulation system status of a healthy individual.

With the method according to an embodiment of the present invention it is possible to detect various states of the blood coagulation system.

A procoagulatory status of an individual's blood coagulation system, i.e. a tendency to thrombosis, is then established when the amount of F1+2 measured in step c) is above the reference value or reference value range that represents a normal blood coagulation system status of a healthy individual. Such a tendency to thrombosis may for example be brought about by circulating preactivated platelets or caused by inadequate therapeutic anticoagulation.

An anticoagulatory status of an individual's blood coagulation system, i.e. a tendency to bleeding, is then established when the amount of F1+2 measured in step c) is below the reference value or reference value range that represents the normal blood coagulation system status of a healthy individual. Such a tendency to bleeding may for example be brought about by a deficiency in coagulation factors or platelets or caused by overly powerful therapeutic anticoagulation.

An exception here is the lupus anticoagulant (LA) test. As is known, this test achieves, at limiting phospholipid concentrations in a test run with a LA-positive sample, the paradoxical detection in vitro of a reduced tendency to coagulation (i.e. a tendency to bleeding or an anticoagulatory status) even though lupus anticoagulant causes an increased tendency to thrombosis in vivo. Similarly, if lupus anticoagulant is present, the method according to an embodiment of the present invention also registers a decrease in the measured amount of F1+2 compared to a normal blood coagulation system status of a healthy individual.

The reaction mixture in step a) is provided by adding to the sample from the individual a coagulation activator to activate the coagulation system.

The phrase "sample from an individual" encompasses in particular body fluids taken from a human or animal individual, primarily platelet-poor or platelet-rich plasma or whole blood.

A "coagulation activator" is to be understood as meaning a substance or substance mixture that brings about activation of the blood coagulation system. Such substances or substance mixtures are well known to those skilled in the art and include for example phospholipids, such as negatively charged phospholipids; lipoproteins, such as thromboplastin; calcium ions; proteins, such as tissue factor; activated serine proteases, such as factor IIa (thrombin), factor VIIa, factor IXa, factor Xa, factor XIa or factor XIIa; snake venoms, such as Protac® enzyme, ecarin, textarin, noscarin, batroxobin, thrombocytin or Russell's viper venom (RVV); contact activators, such as silica, kaolin, ellagic acid, Celite, DNA, RNA or polyphosphates.

The coagulation activator may be an activator of the plasmatic coagulation system, preferably selected from the group comprising thromboplastin, factor IIa, factor VIIa, factor IXa, factor Xa, factor XIa, factor XIIa, snake venoms, negatively charged phospholipids, calcium ions, tissue factor (synonym: factor III), silica, kaolin, ellagic acid, Celite, and polyphosphates.

The coagulation activator may also be a platelet activator, preferably selected from the group comprising ADP, epinephrine, collagen, thrombin-receptor-activating peptide (TRAP), thromboxane A2 mimic U46619, arachidonic acid, ristocetin, thrombin, von Willebrand factor, collagen-related peptide (GPVI stimulation), convulxin, calcium ionophore A23187, and phorbol 12-myristate 13-acetate.

The coagulation activator may in addition be a chemical or physical factor that heightens the procoagulatory properties of erythrocytes, for example the release therefrom of ADP and thromboxane A2, which in turn results in platelet activation (Alamin, A. A. (2021) The role of red blood cells in hemostasis. Semin Thromb Hemost 2021; 47: 26-31) or else brings about the presentation of phosphatidylserine surfaces, which have a procoagulatory effect (Litvinov, R. I. and Weisel, J. W. (2017) Role of red blood cells in hemostasis and thrombosis. ISBT Sci Ser. 2017 February; 12(1): 176-183).

In addition, the coagulation activator may be a substance that activates leukocytes, for example proinflammatory cytokines (TNF-α, IL-8), which induce cell death in neutrophils ("NETosis") and lead to the formation of neutrophil extracellular traps, which have a strongly prothrombotic effect (Kapoor, S. et al. (2018) The role of neutrophils in thrombosis. Thromb Res. 2018 October; 170: 87-96).

Coagulation activators also include activating antibodies in the plasmatic and cellular systems.

To suppress the formation of fibrin in the reaction mixture initiated by activation of the blood coagulation cascade, which could cause turbidity to develop in the reaction mixture and consequently interfere with optical measurements, a fibrin polymerization inhibitor may in a preferred embodiment be added to the reaction mixture. Suitable fibrin polymerization inhibitors are for example oligopeptides that inhibit the stacking (polymerization) of fibrin monomers that develops under the effect of thrombin, thereby preventing clot formation. Particularly suitable oligopeptides are those having the general peptide sequence GPRP—X—NH2, where G is the amino acid glycine, P the amino acid L-proline, R the amino acid L-arginine, and X is alanine or glycine (see for example EP-B1-456152).

The reaction mixture obtained by adding the coagulation activator to the sample is incubated. Preferably, the reaction mixture in step b) is incubated for a period of from 5 seconds to 60 minutes, preferably from 5 to 20 minutes. The incubation period comprises the time interval from the addition of the coagulation activator to the sample up to the point in time at which the coagulation reaction in the reaction mixture is essentially stopped, for example by adding a diluent, for example a large volume of buffer solution or of reagent liquids for the determination of F1+2 (see below), which results in dilution of the reaction mixture to an extent sufficient to halt the coagulation reaction that is taking place in the reaction mixture. Alternatively, the coagulation reaction in the reaction mixture may be arrested by adding a coagulation inhibitor, preferably a coagulation inhibitor from the group comprising factor Xa inhibitors (for example rivaroxaban, edoxaban, apixaban, betrixaban, heparin-antithrombin complex), factor Va inhibitors (for example activated protein C), and calcium chelators (for example EDTA).

Preferably, the reaction mixture is diluted after the incubation in step b) and the quantitative determination of the amount of F1+2 in step c) carried out in the reaction mixture thus diluted.

The reaction mixture is preferably diluted 1:10 to 1:400, very preferably the dilution ratio is 1:40 to 1:200.

The substantial dilution of the reaction mixture or the addition of a coagulation inhibitor largely arrests the formation of further F1+2 peptide. A slight continuation of F1+2 formation could then result in errors if the time from dilution of the reaction mixture or from addition of a coagulation inhibitor up to the start of the F1+2 determination is overall too long or is of varying length from one reaction run (samples, controls, calibrators) to the next. Preferably, the time between dilution of the reaction mixture or halting F1+2 formation and determination of the amount of F1+2 is in every measurement equally long and is less than 2 minutes (max. 10% relative difference between individual determinations).

A further advantage that arises through determining F1+2 in substantial dilutions of reaction mixtures is that any optical interfering factors, such as turbidity caused by blood cells in whole blood, is eliminated.

Preferably, the quantitative determination of the amount of F1+2 in the reaction mixture or in the diluted reaction mixture in step c) is carried out using a F1+2-specific immunoassay.

The quantitative determination of the amount of F1+2 in the reaction mixture or in the diluted reaction mixture can be accomplished in a variety of ways. The prior art describes a number of immunoassays for the quantitative determination of the prothrombin fragment F1+2. The prothrombin fragment F1+2 is a cleavage product of prothrombin, which in turn is the proenzyme of thrombin. The prothrombin protein is modular in structure and consists of an N-terminal F1+2 component and a C-terminal thrombin component. The proteolytic activity of factor Xa results in the cleavage of prothrombin, with each molecule of prothrombin (70 kD) giving rise to a molecule of thrombin (30 kD) accompanied by the release of a prothrombin fragment F1+2 (35-37 kD). The autocatalytic cleavage of prothrombin by thrombin can in addition result in cleavage of the fragments F1 (23 kD) and F2 (14 kD). Since thrombin is not present in vivo in the free form in blood, but undergoes binding to inhibitors and to fibrin immediately after its formation, the extent of in-vivo thrombin formation is detected indirectly, for example by determining the activation marker F1+2. One option for detecting or for excluding elevated thrombin formation in vivo is accordingly the determination of the F1+2 concentration in plasma. The immunoassay described in the prior art for the quantitative determination of the prothrombin fragment F1+2 generated in vivo is likewise suitable for the determination according to embodiments of the present invention of the reaction mixture produced by addition of a coagulation activator, i.e. of the amount of F1+2 formed in vitro.

In one embodiment of the method according to the present invention, the F1+2-specific immunoassay comprises the use of a first antibody having specificity for F1+2 and the use of a second, F1+2-binding antibody.

Immunoassays for the quantitative determination of the prothrombin fragment F1+2 typically comprise at least one F1+2-specific antibody that does not bind to uncleaved prothrombin. The production and use of such a specific anti-F1+2 antibody that does not bind to prothrombin is described for example in EP 303983-A2 (Pelzer et al.), in U.S. Pat. No. 5,830,681 (Hursting et al.) or in US 2003/0219845 A1 (Ruiz et al.). It is important for the specificity of the anti-F1+2 antibody that the antibody binds to an epitope comprising at least the four carboxy terminal amino acids of the F2/F1+2 fragments (Ile-Glu-Gly-Arg-OH). Since it is usually sandwich immunoassays that are used for determination of the F2/F1+2 concentration, two anti-F2/F1+2 antibodies are necessary. EP 1541676-A1 (Teigelkamp et al.) describes antibodies that bind to an epitope on the N-terminal half of the F2 fragment and thus also to intact prothrombin, but are particularly suitable for use as secondary antibodies in combination with the F2/F1+2-neoepitope-specific primary antibodies in a sandwich immunoassay.

The known antibodies are suitable for the determination of the F1+2 concentration in a heterogeneous immunoassay, preferably in the form of a sandwich ELISA method. For this, the F1+2-neoepitope-specific antibodies ("primary antibodies") are coupled to a solid phase and incubated with the sample or, in accordance with embodiments of the present invention, with a reaction mixture, with the result that the F1+2 peptides are able to bind to the immobilized antibodies. A wash step removes unbound proteins, in particular prothrombin, prior to application of the second, F1+2- and prothrombin-binding antibody ("secondary antibody") through addition of an antibody solution. This second antibody is usually associated with a signal-forming component that allows quantification of the amount of F1+2.

In another embodiment of the method according to the present invention, the F1+2-specific immunoassay comprises the use of a first antibody having specificity for F1+2 and the use of a second antibody having specificity for the immune complex consisting of F1+2 and the first antibody.

A F1+2-specific immunoassay of this kind is described in EP 2168985-A1 (Althaus et al.). This describes an antibody that binds specifically to an immune complex that comprises prothrombin fragment F1+2 to which is bound an antibody or antibody fragment having specificity for the carboxy terminal neoepitope of the prothrombin fragment F1+2, but wherein the antibody does not bind to the prothrombin fragment F1+2 or F2 alone and not to the antibody or antibody fragment having specificity for the carboxy terminal neoepitope of the prothrombin fragment F2/F1+2 alone. This assay format ensures specificity high enough to permit the performance of a direct, homogeneous sandwich immunoassay without wash or separation steps.

In a preferred embodiment of the method according to the present invention, the F1+2-specific immunoassay comprises the use of a first antibody having specificity for F1+2 and the use of a second, F1+2-binding antibody, wherein the first and second antibodies are each associated with a particulate solid phase and the quantitative determination of the amount of F1+2 comprises the following steps:

i. mixing the reaction mixture with the particulate solid phases associated with the first and second antibodies and
ii. measuring the agglutination of the particulate solid phases in the reaction mixture.

The term "particulate solid phase" is for the purposes of the present invention to be understood as meaning non-cellular particles having an approximate diameter of at least 20 nm and not more than 20 μm, normally between 200 nm and 350 nm, preferably between 250 and 320 nm, particularly preferably between 270 and 290 nm, very particularly preferably 280 nm. The microparticles may be regular or irregular in shape. They may be spheres, spheroids, or spheres having cavities or pores of varying size. The microparticles may consist of organic material, inorganic material or of a mixture or combination of both. They may consist of a porous or non-porous, swellable or non-swellable material. In principle the microparticles may have any density, but preference is given to particles having a density close to that of water, such as about 0.7 to about 1.5 g/mL. The preferred microparticles are suspendable in aqueous solutions and stable in suspension for as long as possible. They may be translucent, partly translucent, or opaque. The microparticles may consist of a plurality of layers, such as for example so-called core-and-shell particles having a core encased by one or more outer layers. The term microparticles encompasses for example dye crystals, metal sols, silica particles, glass particles, and magnetic particles. Preferred microparticles are particles that are suspendable in aqueous solutions and composed of water-insoluble polymer material, especially of substituted polyethylenes. Very particular preference is given to latex particles, for example composed of polystyrene, acrylic acid polymers, methacrylic acid polymers, acrylonitrile polymers, acrylonitrile-butadiene-styrene, polyvinyl acetate-acrylate, polyvinylpyridine or vinyl chloride-acrylate. Of particular interest are latex particles having reactive groups on their surface, for example carboxyl, amino or aldehyde groups, that permit covalent bonding of the F1+2-binding antibodies to the latex particles.

If F1+2 peptides are present in the reaction mixture, these bind to the F1+2-binding antibodies, thereby bringing about agglutination of the particulate solid phase.

The agglutination of the particulate solid phase in the reaction mixture can be measured photometrically, for example turbidimetrically or nephelometrically. Binding tests based on the principle of particle-enhanced light scattering have been known since about 1920 (for a review, see Newman, D. J. et al., Particle enhanced light scattering immunoassay. Ann Clin Biochem 1992; 29: 22-42). Preference is in this context given to polystyrene particles having a diameter of 0.1 to 0.5 μm, more preferably having a diameter of 0.15 to 0.35 μm. Preference is given to using polystyrene particles having amine, carboxyl or aldehyde functions. Preference is also given to using core-and-shell particles. The synthesis of the particles and the covalent coupling of ligands is described for example in Peula, J. M. et al., Covalent coupling of antibodies to aldehyde groups on polymer carriers. Journal of Materials Science: Materials in Medicine 1995; 6: 779-785.

Alternatively, the agglutination of the particulate solid phase in the reaction mixture can be measured by measuring a signal generated by a signal-forming system when the first and the second component of the signal-forming system are brought into spatial proximity. In this context, the first antibody is associated with a first particulate solid phase and the second antibody is associated with a second particulate solid phase, wherein the first particulate solid phase is associated with a first component of a signal-forming system and the second particulate solid phase is associated with a second component of a signal-forming system, and wherein the first and the second component of the signal-forming system interact with one another such that this produces a detectable signal when the first and the second component of the signal-forming system are brought into spatial proximity and the agglutination of the particulate solid phases in the reaction mixture is measured on the basis of the signal produced.

In this embodiment of the method according to the present invention, the signal-forming system comprises at least a first and a second component, which interact such that a detectable signal is produced when they are brought into spatial proximity and are thereby able to interact with one another. An interaction between the components is to be understood as meaning in particular an energy transfer, i.e. the direct transfer of energy between the components, for example through irradiation with light or electrons or via reactive chemical molecules such as short-lived singlet oxygen. The energy transfer may be from one component to the other, but a cascade of different substances via which the energy transfer proceeds is also possible. For example, the components may be a pair comprising an energy donor and an energy acceptor, for example a photosensitizer and a chemiluminescent agent (EP-A2-0515194, LOCI® Technologie) or a photosensitizer and fluorophore (WO 95/06877) or radioactive iodine-125 and fluorophore (Udenfriend et al. (1985) Proc. Natl. Acad. Sci. 82: 8672-8676) or fluorophore and fluorescence quencher (U.S. Pat. No. 3,996,345). Particularly preferably, the first component of the signal-forming system is a chemiluminescent agent and the second component of the signal-forming system is a photosensitizer or vice-versa, and it is the chemiluminescence in the reaction mixture that is measured.

In a further embodiment, the principle of which is known under the abbreviation HISCL, a first antibody having specificity for F1+2 is first contacted with the sample, allowing rapid binding to F1+2 to take place. Bound to the first antibody is a factor (for example biotin) that binds to a binding partner (for example streptavidin) present on the surface of magnetic particles. These magnetic particles are added in a second step. After the binding of the antibody-F1+2 complex to the particles has taken place, the particles are bound to the surface of the cuvette by magnetic forces and the rest of the reaction mixture is removed by wash steps. After this, a second, F1+2-binding (and optionally prothrombin-binding) antibody is contacted with the magnetic particles.

Alternatively, it is also possible to use at this point the antibody from EP 2168985-A1 (Althaus et al.), which is directed against the immune complex obtained from the anti-F1+2 antibody and F1+2. After further wash processes and the chemiluminescence method known to those skilled in the art, the amount of F1+2 in the test run is determined.

A further embodiment of the HISCL method with ultra-high sensitivity is the immune complex transfer method. The first step in this method is the formation of a complex from magnetic particles bound to a F1+2 antigen-antibody complex and an antibody bound thereto that contains a detection enzyme (for example alkaline phosphatase, ALP). After the washing processes, the chemiluminescence detection is not performed directly; instead, the binding between magnetic particles and anti-F1+2 antibody is broken down. The broken-down complex is transferred to another cuvette, leaving the magnetic particles behind in the first cuvette. Present in the second cuvette are further magnetic particles that bind to the complex. After further wash processes and the chemiluminescence method known to those skilled in the art, the amount of F1+2 in the test run is determined.

The result of the quantitative determination of the amount of F1+2 in step c) of the method according to embodiments of the present invention can be represented for example in the form of a raw value for the measured signal of the respective determination method (e.g. kilocounts [kcnt]). Alternatively, the result can also be expressed as a concentration, in which case the raw value for the measured signal is converted into a F1+2 concentration (e.g. pmol/L) by a F1+2 calibrator having a known F1+2 concentration. The use of calibrators having normal or procoagulatory or anticoagulatory properties allows either the raw value for the measured signal or the derived concentration to be converted into % of norm.

The blood coagulation system status is finally established according to embodiments of the present invention by comparing the amount of F1+2 thus measured in the reaction mixture with a reference value or reference value range that represents the normal blood coagulation system status of a healthy individual (step d)).

A suitable reference value is the amount of F1+2 measured with the same method (or measured beforehand) in reaction mixtures comprising samples from individuals or samples of pooled samples from a plurality of individuals known to have a normal blood coagulation system status. For the determination of a reference value or reference value range in a large number of samples from healthy donors known to have a normal blood coagulation system status, the amount of F1+2 in the reaction mixture is normally measured and then compared with the amount of F1+2 in a large number of samples from donors having a known procoagulatory blood coagulation system status and/or from donors having a known anticoagulatory blood coagulation system status. A reference value may for example then be a limit value that permits differentiation of individuals having a normal blood coagulation system status from individuals having a procoagulatory blood coagulation system status or differentiation of individuals having a normal blood coagulation system status from individuals having an anticoagulatory blood coagulation system status. If the measured amount of F1+2 in a reaction mixture is above the predetermined reference value, this makes it possible to detect a procoagulatory status in the individual's blood coagulation system; if the measured amount of F1+2 in a reaction mixture is less than the predetermined reference value, this makes it possible to detect an anticoagulatory status in the individual's blood coagulation system. The described reference values may be the upper and lower limits of a reference value range that indicates a range for the measured amount of F1+2 in a reaction mixture that corresponds to a normal blood coagulation system status of an individual.

In a particular embodiment of the method according to embodiments of the present invention, the sample in a second test run undergoes an additional determination of the amount of F1+2 in the sample without the sample being contacted with a coagulation activator, i.e. without the induction in the sample of thrombin formation and thus of the formation of F1+2. For this, the sample is mixed with a buffer instead of the coagulation activator and is then incubated and diluted in the same way as in the test run according to embodiments of the present invention. The amount of F1+2 thus determined corresponds to the amount of F1+2 already present in the sample without activation of coagulation. Calculating the difference between the test results from the first test run (with coagulation activator) and the test result from the second test run (without coagulation activator) prevents the possibility of high levels of F1+2 already present in the sample without addition of a coagulation activator from being misidentified as an elevated in-vitro F1+2-generation capacity.

Embodiments of the present invention also provide a test kit for establishing the blood coagulation system status of an individual, the test kit comprising at least the following components:

A. a reagent comprising a coagulation activator and
B. one or more reagents for the quantitative determination of F1+2.

The reagent comprising coagulation activator comprises one of the other substances described hereinabove, or a mixture of substances, that brings about activation of the blood coagulation system. The reagent comprising coagulation activator is provided for the purposes of providing the reaction mixture containing the body fluid sample of the individual.

The one or more reagents for the quantitative determination of F1+2 comprise F1+2-binding antibodies (as described hereinabove) and components of a signal-forming system (likewise as described hereinabove). The one or more reagents for the quantitative determination of F1+2 are provided for the quantitative determination of the amount of in-vitro-generated F1+2 in the reaction mixture obtained from the body fluid sample of the individual and reagent comprising coagulation activator.

The reagents of the test kit according to embodiments of the present invention may be provided in liquid or lyophilized form. Where some or all of the reagents of the test kit are present in the form of lyophilizates, the test kit may additionally include the solvent required for reconstitution of the lyophilizates, for example distilled water or appropriate buffers.

Suitable controls or calibrators for the method according to embodiments of the present invention are samples of plasma or whole blood having a defined prothrombin concentration. The production of control/calibrator materials of this kind is described for example in EP 1544621-A1.

In one embodiment, a test kit according to the present invention additionally includes C. a first calibrator material that represents a normal blood coagulation system status of a healthy individual, and optionally
D. at least a second calibrator material that represents a procoagulatory or an anticoagulatory blood coagulation system status of an individual.

The calibrator material that represents a normal blood coagulation system status of a healthy individual may consist for example of a plasma pool from a plurality of healthy donors ("normal plasma").

The calibrator material that represents a procoagulatory blood coagulation system status of an individual may consist for example of a plasma pool from a plurality of healthy donors or a plurality of donors having the prothrombin mutation G20210A to which has been added defined amounts of one or more coagulation factors (for example prothrombin, factor V, factor X).

The calibrator material that represents an anticoagulatory blood coagulation system status of an individual may consist for example of a plasma pool from a plurality of healthy donors diluted with buffer or of a prothrombin-deficient plasma or of a mixture of various deficient plasmas.

DETAILED DESCRIPTION

EXAMPLES

Figure 1:
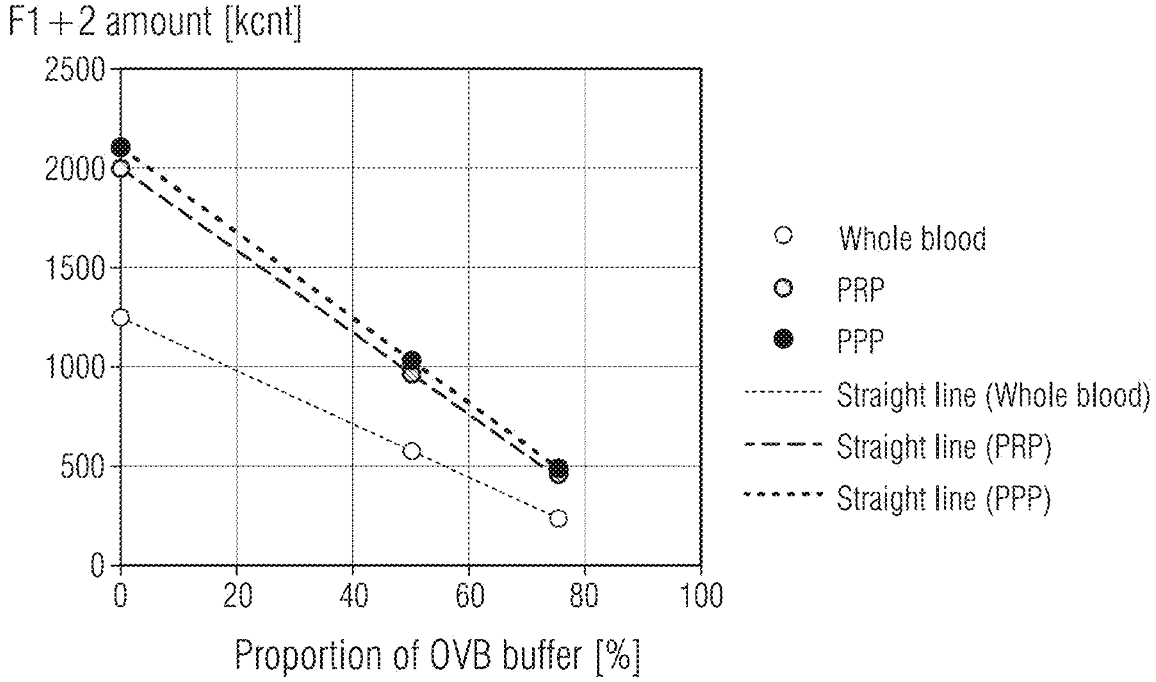
FIG. 1 shows a diagram in which the linear relationship between the measured amount of F1+2 [kcnt] and dilution (undiluted, 1:2 and 1:4) in the various sample types (whole blood, platelet-rich plasma (PRP), platelet-poor plasma (PPP)) is made clear.

Example 1: Determination of the Amount of In-Vitro-Generated F1+2 Peptide in Plasma Samples and Whole Blood Samples Samples of whole blood or plasma (PRP or PPP) were mixed with the components of the Innovance ETP assay (Siemens Healthcare Diagnostics Products GmbH, Germany) as follows:

87 μL ETP buffer
+40 μL ETP reagent
265 seconds incubation
+108 μL sample
440 seconds incubation
+15 μL Innovin reagent (lipidated tissue factor; Siemens Healthcare Diagnostics Products GmbH, Germany)
+10 μL ETP $CaCl_2$) solution
20 minutes incubation at 37° C.
1:100 dilution of the reaction mixture by addition of Owren's Veronal Buffer (OVB buffer).
5 μL of the diluted reaction mixture was mixed with
a first reagent ("reagent BA") comprising a first, biotinylated monoclonal antibody having specificity for the neoepitope of F1+2; and then
with a second reagent ("Chemibeads reagent") comprising a second monoclonal antibody having specificity for the immune complex consisting of the first antibody and F1+2 peptide bound thereto, which is coupled to latex particles associated with a chemiluminescent compound (Chemibeads); and
with a third reagent ("Sensibeads" reagent) comprising streptavidin-coated latex particles associated with a photosensitizer (Sensibeads).

After further incubation of the reaction run for a period of 6 minutes, the chemiluminescence signal in the arbitrary unit kilocounts (kcnt) was measured.

The LOCI® technology used here is based on a chemiluminescent compound coupled to latex particles (Chemibeads, CB) and a photosensitizer coupled to latex particles (Sensibeads, SB) being brought into spatial proximity by binding to an analyte (here: F1+2 peptide), with the result that singlet oxygen generated by the photosensitizer is able to excite the chemiluminescent compound. The amount of chemiluminescence generated correlates with the amount of analyte.

This was used to investigate samples from three apparently healthy normal donors. Each sample underwent a duplicate determination and all results were averaged (Table 1). The results show that, in the presence of tissue factor, lipids, and $CaCl_2$) from the Innovance ETP reagents and without addition of a platelet activator, the F1+2 generation potential in PRP and PPP is almost equally high. Since the hematocrit of 36 to 53% (normal range in men and women) means that the actual plasma volume in whole blood available for the measurement of F1+2 is only 47 to 64%, the value of 1242 kcnt determined in whole blood is very plausible when set alongside the value of 2111 kcnt determined in plasma. At the same time, this demonstrates that the high dilution ensures that the turbidity caused by the high platelet count in PRP and by the high total cell count in whole blood does not substantially interfere with the F1+2 determination.

TABLE 1

| Sample | F1 + 2 amount [kcnt] |
|---|---|
| Whole blood | 1242 |
| PRP | 2009 |
| PPP | 2111 |

To investigate the dependence of the amount of in-vitro-generated F1+2 on the available coagulation factors, the samples were prediluted 1:2 and 1:4 with OVB buffer (Table 2).

TABLE 2

| Donor | Sample | Dilution | F1 + 2 amount [kcnt] 1 | F1 + 2 amount [kcnt] 2 | Mean value [kcnt] | SD [kcnt] | CV (%) |
|---|---|---|---|---|---|---|---|
| 1 | Whole blood | 1:1 | 1367 | 1517 | 1442 | 106.0 | 7.3 |
| | | 1:2 | 622 | 615 | 618 | 4.9 | 0.8 |
| | | 1:4 | 298 | 291 | 294 | 5.1 | 1.7 |
| 2 | | 1:1 | 1213 | 1278 | 1246 | 45.8 | 3.7 |
| | | 1:2 | 538 | 473 | 505 | 45.8 | 9.1 |
| | | 1:4 | 231 | 217 | 224 | 10.1 | 4.5 |
| 3 | | 1:1 | 1041 | 1033 | 1037 | 5.8 | 0.6 |
| | | 1:2 | 481 | 485 | 483 | 3.2 | 0.7 |
| | | 1:4 | 218 | 215 | 217 | 2.0 | 0.9 |
| 1 | PRP | 1:1 | 2379 | 2498 | 2439 | 84.2 | 3.5 |
| | | 1:2 | 1172 | 1083 | 1127 | 62.9 | 5.6 |
| | | 1:4 | 521 | 561 | 541 | 28.4 | 5.2 |
| 2 | | 1:1 | 1984 | 1901 | 1942 | 58.7 | 3.0 |
| | | 1:2 | 957 | 895 | 926 | 44.2 | 4.8 |
| | | 1:4 | 451 | 407 | 429 | 31.0 | 7.2 |
| 3 | | 1:1 | 1689 | 1603 | 1646 | 60.8 | 3.7 |
| | | 1:2 | 728 | 774 | 751 | 32.0 | 4.3 |
| | | 1:4 | 372 | 356 | 364 | 11.2 | 3.1 |

TABLE 2-continued

| Donor | Sample | Dilution | F1 + 2 amount [kcnt] 1 | 2 | Mean value [kcnt] | SD [kcnt] | CV (%) |
|---|---|---|---|---|---|---|---|
| 1 | PPP | 1:1 | 2705 | 2478 | 2592 | 160.9 | 6.2 |
| | | 1:2 | 1404 | 1215 | 1309 | 133.3 | 10.2 |
| | | 1:4 | 592 | 574 | 583 | 13.2 | 2.3 |
| 2 | | 1:1 | 2044 | 1888 | 1966 | 110.5 | 5.6 |
| | | 1:2 | 951 | 942 | 947 | 5.9 | 0.6 |
| | | 1:4 | 451 | 423 | 437 | 19.7 | 4.5 |
| 3 | | 1:1 | 1865 | 1687 | 1776 | 125.8 | 7.1 |
| | | 1:2 | 884 | 822 | 853 | 44.3 | 5.2 |
| | | 1:4 | 404 | 379 | 391 | 17.3 | 4.4 |

In all three sample types, a linear relationship was found between the content in the sample (i.e. content of coagulation factors) and the amount of in-vitro-generated F1+2. This confirms the dilution linearity of the test results and, in the case of whole blood and PRP as sample, hence also the absence of potential interferences brought about solely by the presence of cells (for example the "inner filter effect") and by the turbidity of the sample (FIG. 1).

Example 2: Comparison of the Inventive F1+2 Generation Assay with a Thrombin Generation Assay (Endogenous Thrombin Potential For the performance of the inventive method for determining the amount of in-vitro-generated F1+2, plasma samples were mixed with the components of the Innovance ETP assay (Siemens Healthcare Diagnostics Products GmbH, Germany) as follows:

108 μL sample
+82 μL ETP buffer
+35 μL ETP reagent
150 seconds incubation at 37° C.
+15 μL Innovin reagent (lipidated tissue factor)
+10 μL ETP $CaCl_2$ solution
20 minutes incubation at 37° C.
1:100 dilution of the reaction mixture by addition of OVB buffer.

As in example 1, 5 μL of the diluted reaction mixture was used for determining the amount of F1+2 formed in the reaction mixture.

Figure 2:
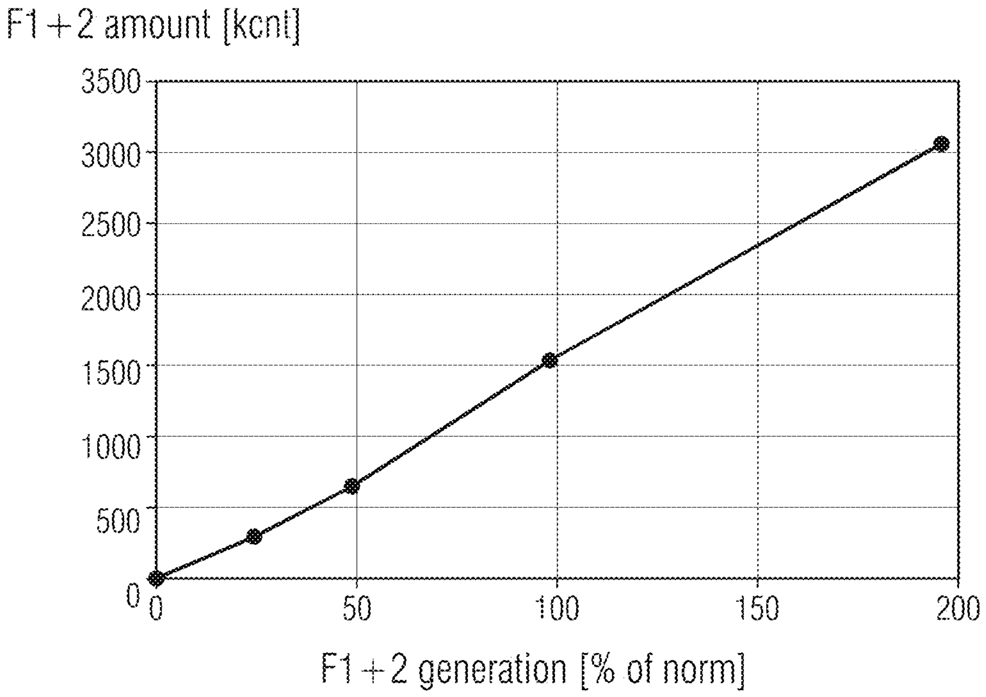
FIG. 2 shows a diagram depicting the calibration curve for the inventive test for determining the amount of in-vitro-generated F1+2.

A calibration of the inventive F1+2 generation assay using a plasma calibrator material having a defined prothrombin content (% of norm) (Innovance ETP standard, Siemens Healthcare Diagnostics Products GmbH, Germany) was additionally carried out. For the determination of the calibration curve (FIG. 2), the standard was diluted with OVB buffer. The highest calibration point at 196% was not measured, but extrapolated.

For comparison with the endogenous thrombin potential (ETP), the plasma samples were additionally measured with the Innovance ETP assay (Siemens Healthcare Diagnostics Products GmbH, Germany). In this known method for determining the ETP, a coagulation activator (Innovin and calcium ions), a chromogenic thrombin substrate, and a fibrin inhibitor are added to the sample and the reaction kinetics of a thrombin substrate are determined photometrically over a period of about 20 minutes. The ETP is determined on the basis of the parameters Cmax (maximum rate of reaction) and AUC (area under the curve) of the measured reaction kinetics. A calibration curve is created using the Innovance ETP standard (Siemens Healthcare Diagnostics Products GmbH, Germany), with the results given units of % of norm. The ETP test undergoes automated processing on the BCS XP analysis system (Siemens Healthcare Diagnostics Products GmbH, Germany).

Figure 3:
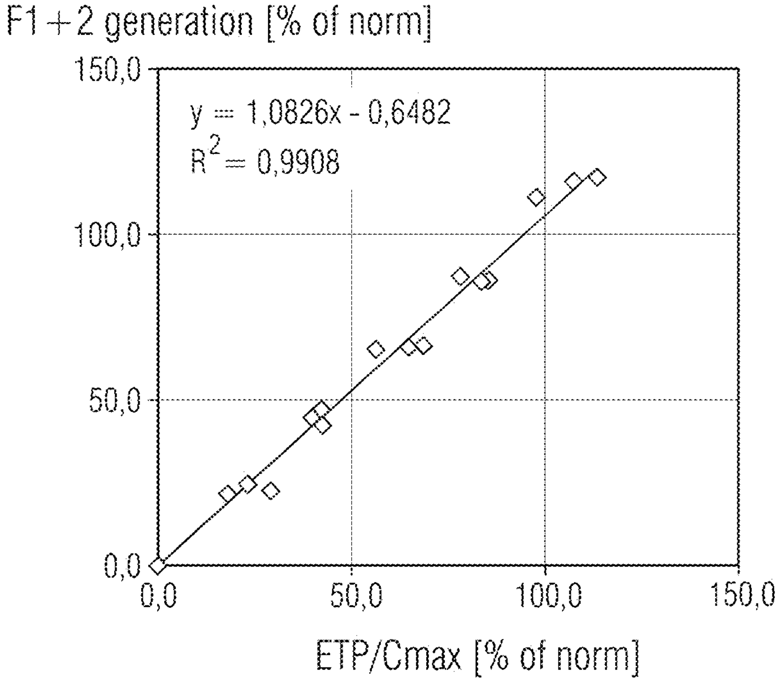
FIG. 3 shows a diagram in which F1+2 generation determined according to an embodiment of the present invention (% of norm) is compared with the ETP (parameter=Cmax; % of norm) in various samples.
Figure 4:
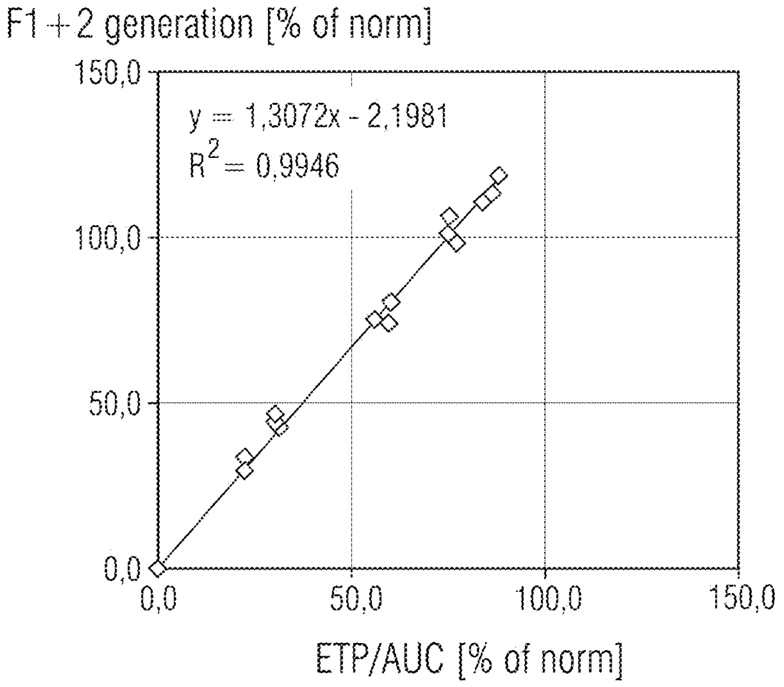
FIG. 4 shows a diagram in which F1+2 generation determined according to an embodiment of the present invention (% of norm) is compared with the ETP (parameter=AUC; % of norm) in various samples.

For the purposes of comparing F1+2 generation and endogenous thrombin potential, plasma samples were produced by diluting a normal plasma pool (mixture of plasmas from a plurality of healthy donors) with a deficient plasma pool (mixture of plasmas from a plurality of healthy donors in which a severe deficiency in a plurality of coagulation factors has been produced by AlOH absorption) in a number of dilution steps. FIGS. 3 and 4 show that, in the ETP test and in the F1+2 generation test the depletion in coagulation factors is manifested in a similar manner in a fall in % of norm values.

This shows that the F1+2 generation test, the measurement principle and evaluation of which are considerably simpler than the measurement principle and evaluation of the endogenous thrombin potential, responds in a similar manner to the loss of coagulation factors and thus detects an anticoagulatory situation in a similar manner to the thrombin generation test.

Example 3: Comparative Determination of Single-Factor Deficiencies by Measuring the F1+2 Generation Potential and Measuring the Endogenous Thrombin Potential (ETP To determine the dependence of the F1+2 generation potential on individual coagulation factors, single-factor deficient samples were produced. This was done by diluting a normal plasma pool with various factor-deficient plasmas (plasmas deficient in factors II, VII, IX, and X) in various dilution steps. These samples were measured both with the Innovance ETP thrombin generation test and with the inventive F1+2 generation test, as per example 2.

Figure 5:
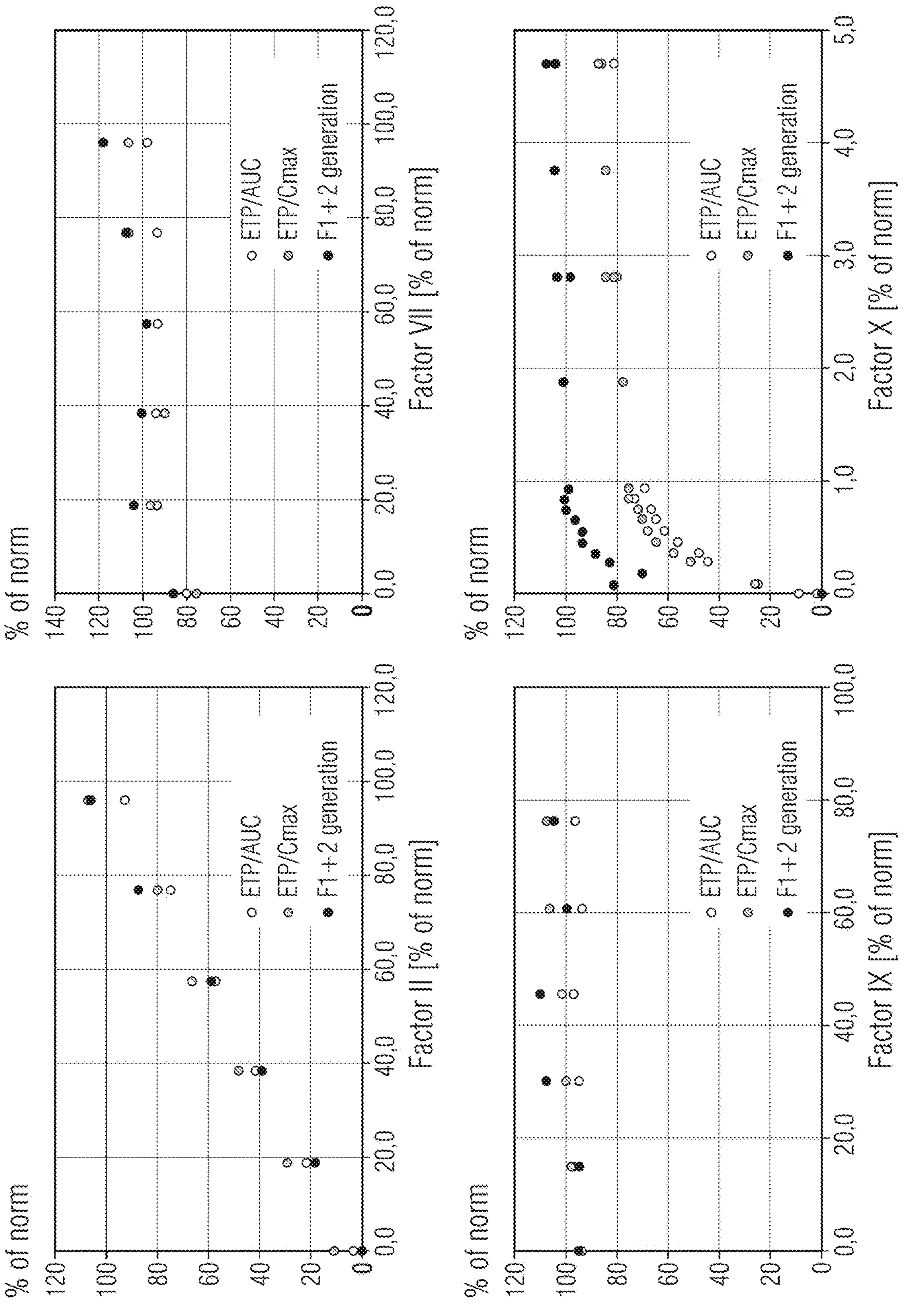
FIG. 5 shows four diagrams in which F1+2 generation determined according to an embodiment of the present invention and the endogenous thrombin potential (ETP) of plasma samples deficient in different coagulation factors (factors II, VII, IX, and X) are compared.

The measured values generally show a fall as a function of the factor concentration in a similar manner both in the thrombin generation test and in the F1+2 generation test (FIG. 5). The dependence of the factor II activity is in both cases very strong and almost linear. A deficiency in factor VII has only a weak effect and becomes noticeable only below 20% of the norm. A deficiency in factor IX did not show any effects at all. Factor X deficiency has an effect only below 1% of the norm, both thrombin generation and F1+2 generation being hindered completely in pure deficient plasma.

The F1+2 generation test thus registers the effects of factor deficiencies just as the thrombin generation test does.

Example 4: Establishment of an Anticoagulatory Blood Coagulation System Status by Determining the Strength of Anticoagulation of a Factor Xa Inhibitor The TF/lipid reagent acting as coagulation activator was prepared as follows: Innovin reagent (see example 1) was diluted 1:98.6 with Owren's Veronal Buffer. To 1493.3 μL of this dilution was added 6.7 μL of a phospholipid suspension (68% 1,2-dioleoyl-sn-glycero-3-phosphocholine, 32% 1-palmitoyl-2-oleoyl-sn-glycero-3-phosphoserine, together 11.4 g/L).

This modified coagulation activator was used to perform the F1+2 generation test as described in example 2.

The anticoagulated samples were produced by same procedure as in the creation of the calibration curve for the Innovance anti-Xa rivaroxaban assay (Siemens Healthcare Diagnostics Products GmbH, Germany). A standard 0 (=normal plasma pool without rivaroxaban) and a standard 1 (normal plasma pool containing 410 ng/mL rivaroxaban) were mixed in various ratios.

The samples were measured using the Innovance anti-Xa rivaroxaban assay, a chromogenic anti-FXa test for determining the concentration of rivaroxaban, and with the inventive F1+2 generation test.

Figure 6:
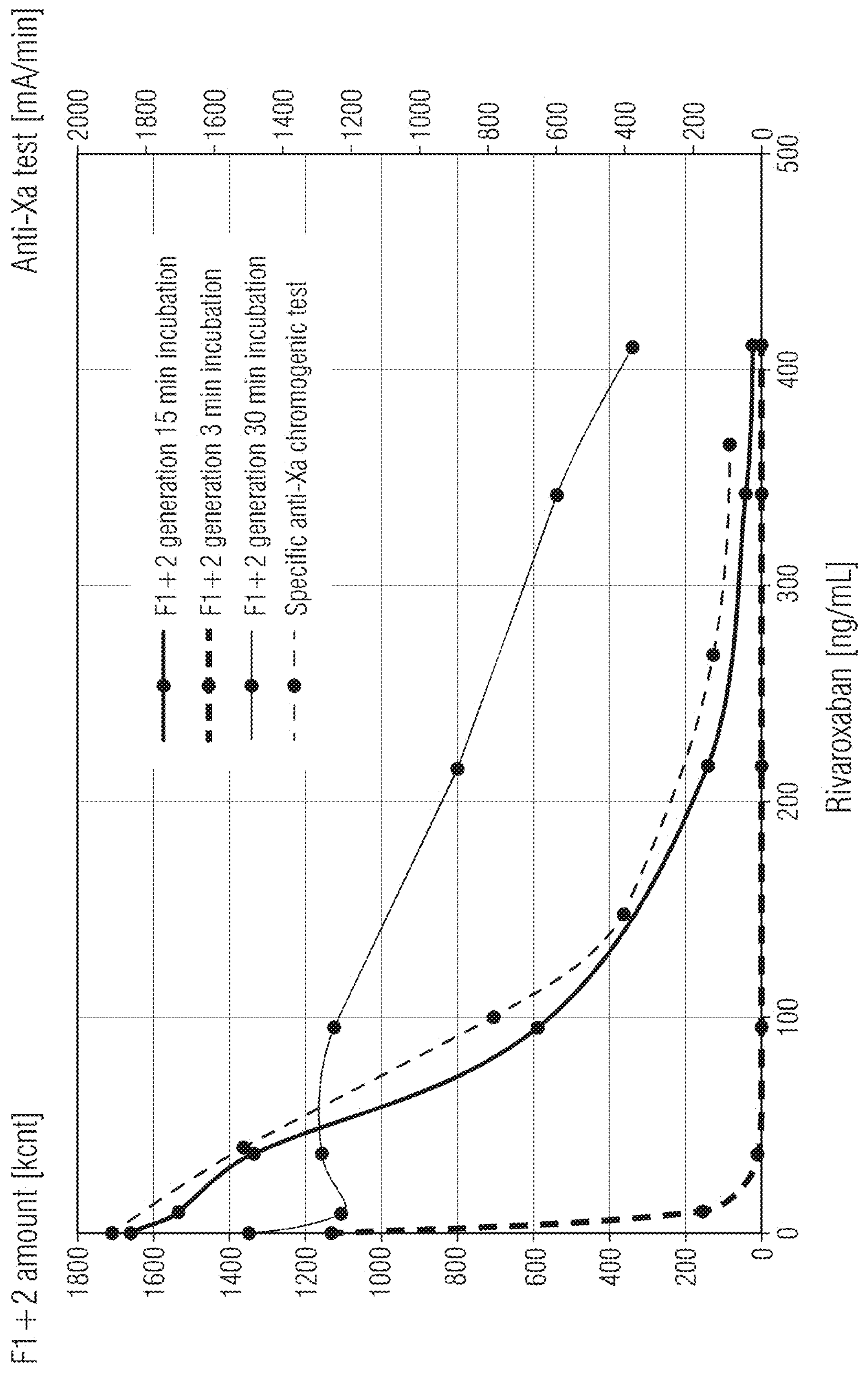
FIG. 6 shows a diagram in which F1+2 generation potential determined according to an embodiment of the present invention with varying incubation times and the amount of rivaroxaban determined with an anti-FXa test are compared in plasma samples having different rivaroxaban concentrations.

In the F1+2 generation test with an incubation time of 15 minutes after addition of $CaCl_2$), a dependence of the signals (kcnt) on the rivaroxaban concentration very similar to that in the specific anti-Xa rivaroxaban test (mA signal) was observed (FIG. 6). The F1+2 generation test can thus likewise be used for quantitation of anticoagulants. Advantageously, the test can very readily achieve a higher sensitivity by shortening the incubation time or a broader measurement range by prolonging the incubation time. With an incubation time of 3 minutes (after addition of $CaCl_2$)) the test responds very sensitively to an increase in the rivaroxaban concentration from 0 to 10 ng/mL. With an incubation time of 30 minutes (after addition of $CaCl_2$)), the measurement range can be extended to over 400 ng/mL. Such a change to the incubation time can be made automatically by the analysis system in the form of a repeat measurement when the initial measurement result is below or above the measurement range.

Example 5: Establishment of an Anticoagulatory Blood Coagulation System Status by Determining the Strength of Anticoagulation of a Factor IIa Inhibitor The TF/lipid reagent acting as coagulation activator was prepared as described in example 4, and the F1+2 generation test performed therewith as described in example 2.

The anticoagulated samples were produced by same procedure as in the creation of the calibration curve for the Innovance DTI assay (Siemens Healthcare Diagnostics Products GmbH, Germany). A standard 0 (=normal plasma pool without dabigatran) and a standard 1 (normal plasma pool containing 548 ng/mL dabigatran) were mixed in various ratios.

The samples were measured using the Innovance DTI assay, a chromogenic anti-FIIa test for determining the concentration of dabigatran.

Figure 7:
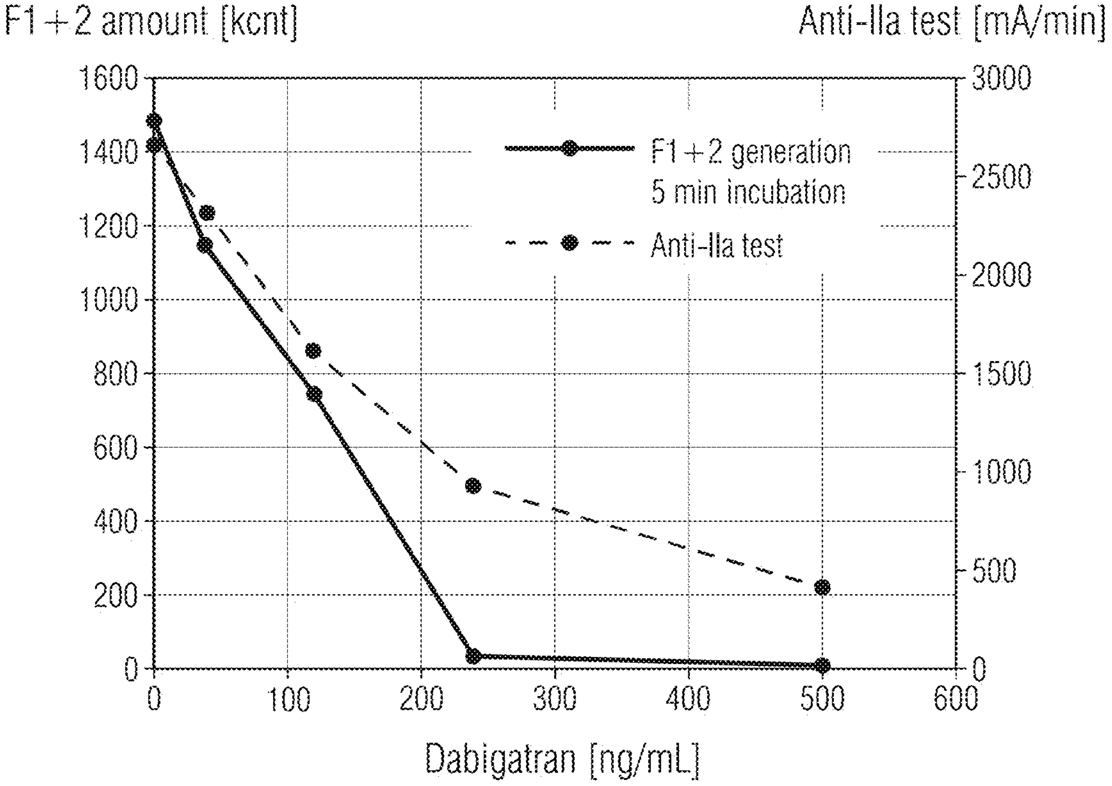
FIG. 7 shows a diagram in which F1+2 generation potential determined according to an embodiment of the present invention and the amount of dabigatran determined with an anti-IIa test are compared in plasma samples having different dabigatran concentrations.
Figure 8:
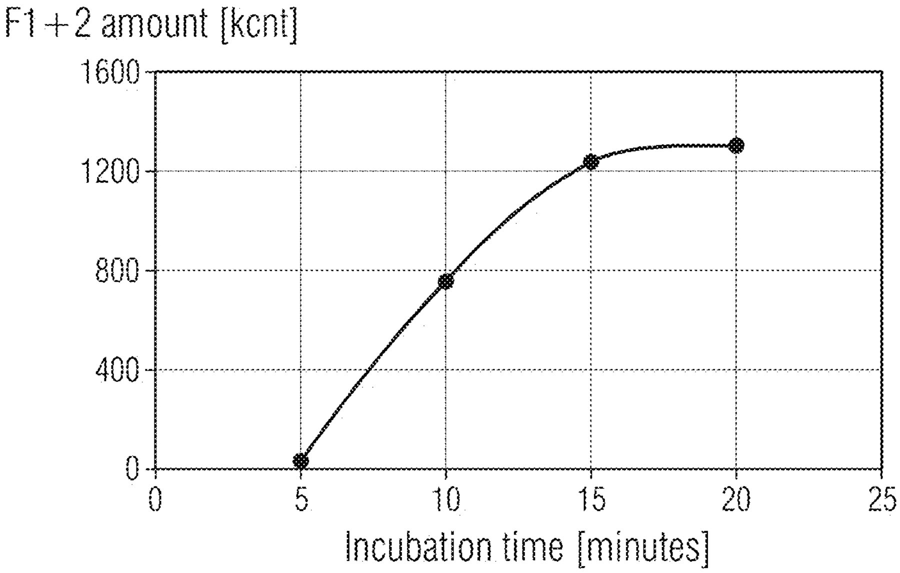
FIG. 8 shows a diagram depicting the F1+2 generation potential determined according to an embodiment of the present invention in a plasma sample containing 120 ng/mL of dabigatran with different incubation times.

In the F1+2 generation test with an incubation time of 5 minutes after addition of $CaCl_2$), a dependence of the signals (kcnt) on the dabigatran concentration very similar to that in the specific anti-IIa dabigatran test (mA/min signal) was observed (FIG. 7). The F1+2 generation test can thus likewise be used for quantitation of anticoagulants. Advantageously, the test can very readily achieve a higher sensitivity by shortening the incubation time or a broader measurement range by prolonging the incubation time (after addition of $CaCl_2$)). FIG. 8 shows the increase in signal height in the F1+2 generation test at a dabigatran concentration of 120 ng/mL resulting from an increase in incubation time. Such a change to the incubation time can be made automatically by the analysis system in the form of a repeat measurement when the initial measurement result is below or above the measurement range.

Example 6: Shortening the Incubation Time in the F1+2 Generation Test

The comparative determination of the amount of in-vitro-generated F1+2 and of the ETP was carried out as described in example 2, except that, in the F1+2 generation test, incubation after the addition of $CaCl_2$) was for only 5 minutes instead of incubation for 20 minutes. The calibration and the production and measurement of the samples (samples with increasing coagulation factor deficiency in % of norm) was carried out as described in example 2.

Figure 9:
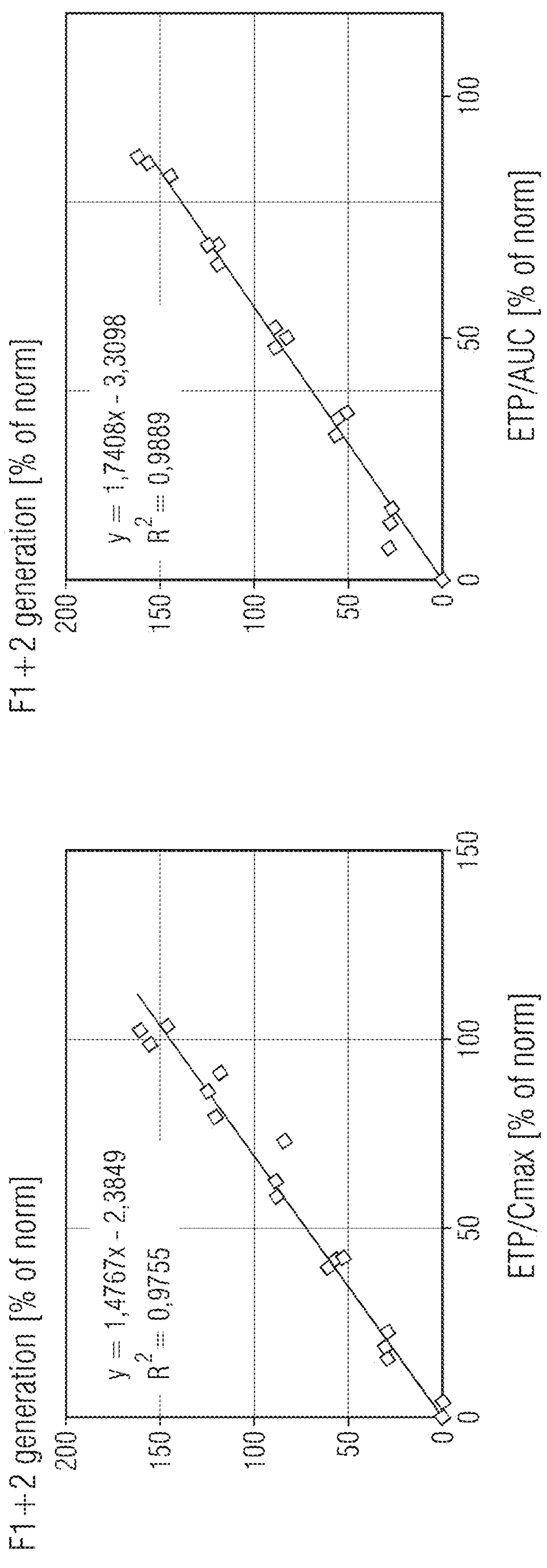
FIG. 9 shows two diagrams in which F1+2 generation determined according to an embodiment of the present invention (% of norm) employing just a 5-minute incubation time after addition of all coagulation factors is compared with the ETP (parameter=Cmax; % of norm, left diagram; parameter=AUC; % of norm, right diagram) in various samples.

The correlation with the classical ETP test of the results of the F1+2 generation test with incubation for 5 minutes remains linear (see FIG. 9). The slope of the lines (significantly greater than 1) points to a need for specific standardization. Since the decrease in the measured values shows the same linear relationship with the decrease in the coagulation factors, decreasing the incubation time is possible. This results in the overall time taken for the F1+2 generation test being shortened by 15 minutes, to 7.5 minutes, which represents a considerable advantage compared to the ETP test of the prior art.

Example 7: Establishment of a Procoagulatory Blood Coagulation System Status by Determining an Increase in Platelet Activation Through Measurement of the F1+2 Generation Potential The detection of a hyper- or hypocoagulatory state arising from dysfunctional thrombin functionality or F1+2 generation functionality in blood cells is possible only when such blood cells are present in the sample. To detect dysfunction in platelet functionality, it is necessary to use either PRP or whole blood as the sample. To detect dysfunction in other blood cells, it is necessary to use whole blood as the sample.

A hypercoagulatory state in the sample (whole blood, PRP or plasma) was achieved by preactivating platelets with collagen. This was done by mixing 900 μL of sample with 100 μL of collagen solution (20 μg/mL), or with 100 μL of OVB buffer for the control, and incubating the mixture for 20 minutes at 37° C. in a water bath.

In order to be able to sensitively detect the influence of the blood cells, the Innovin reagent, which comprises tissue factor and lipid, was diluted 1:780 with OVB buffer.

The preactivated samples were mixed with the components of the Innovance ETP assay (Siemens Healthcare Diagnostics Products GmbH, Germany) as follows:

108 μL sample
+40 μL ETP buffer
+35 μL ETP reagent
150 seconds incubation
+10 μL Innovin reagent (prediluted 1:780 with OVB)
+14 μL ETP $CaCl_2$)
30 minutes incubation at 37° C.
1:100 dilution of the reaction mixture with OVB buffer.

As in example 1, 5 μL of the diluted reaction mixture was used for determining the amount of F1+2 formed in the reaction mixture.

Figure 10:
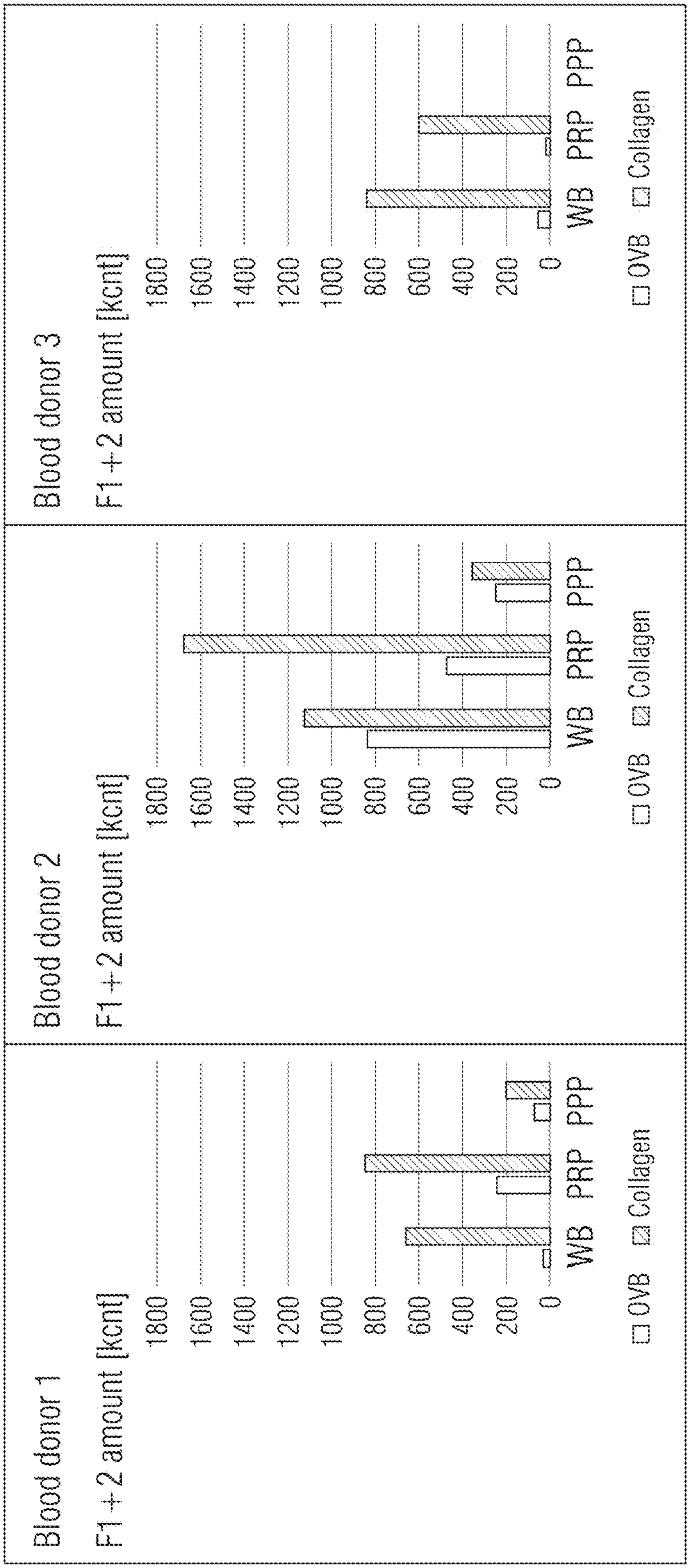
FIG. 10 shows diagrams depicting F1+2 generation determined according to an embodiment of the present invention (kcnt) in collagen-preactivated samples of whole blood (WB), PRP, and PPP from three blood donors.

Three seemingly healthy blood donors were investigated. When using PRP or whole blood as sample, preactivation of the platelets could be demonstrated in whole blood and PRP by the substantial increase in F1+2 generation compared to non-preactivated platelets (addition of OVB buffer instead of collagen) (see FIG. 10). Measurement of the F1+2 generation potential in whole blood or PRP can thus be used to demonstrate hypercoagulability of cellular origin and thus a procoagulatory blood coagulation system status.

Blood donor 2 is unusual in having a particularly high F1+2 generation potential, which is already clear without collagen activation of the platelets and even in plasma as sample. This indicates the in-vivo presence in this donor of a procoagulatory blood coagulation system status.

Example 8: Establishment of an Anticoagulatory Blood Coagulation System Status by Determining the Anticoagulatory Effect of a Reduced Platelet Count PRP and PPP samples from three apparently healthy blood donors were prepared and the platelet count determined.

Figure 11:
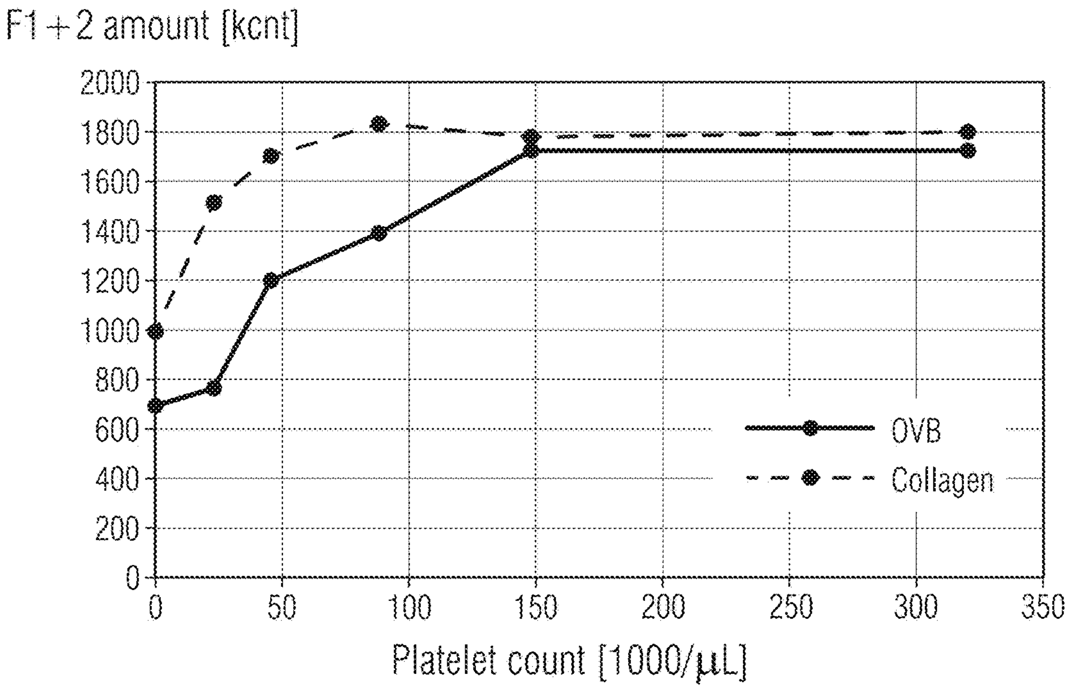
FIG. 11 shows a diagram depicting F1+2 generation determined according to an embodiment of the present invention (kcnt) in collagen-preactivated plasma samples having different platelet counts.

The F1+2 generation potential was measured with PRP as sample and with and without preactivation through addition of collagen as described in example 7, the collagen solution here having a concentration of 80 μg/mL. The results of the samples from the three blood donors were averaged. Below a platelet count of <100 000/μL the F1+2 generation potential decreases when the platelets are not preactivated. When the platelets are preactivated, the F1+2 generation potential decreases below a platelet count of <50 000/μL (see FIG. 11).

Measurement of the F1+2 generation potential therefore indicates an anticoagulatory blood coagulation system status caused by thrombocytopenia. The results for the F1+2 generation reflects the situation in vivo, in which thrombocytopenia has less of an effect when the platelets present are particularly active.

Example 9: Establishment of an Procoagulatory Blood Coagulation System Status by Determining the Procoagulatory Effect of Lupus Anticoagulant The most commonly used test for the determination of lupus anticoagulant (LA) is the DRVVT test (dilute Russell's viper venom test). In this test, coagulation is triggered using RVV as coagulation activator. First of all, a test is carried out in which the coagulation activator reagent has only a very low phospholipid content (LA1 test). If lupus anticoagulant is present, the coagulation time in the LA1 test is lengthened. This is followed by the performance of a second test (LA2) using a coagulation activator reagent that has a higher phospholipid concentration. The LA2 test also then shows an approximately normal coagulation time when lupus anticoagulant is present. A LA2/LA1 ratio for the two tests is close to 1 when a normal sample is measured and falls below 1 when lupus anticoagulant is present.

The lupus anticoagulant test was carried out in the standard manner but with the difference that, instead of the measurement of the coagulation time, the amount of F1+2 formed in the reaction mixture was determined (see example 1).

Performance of the LA1 Test:

100 μL sample
240 seconds incubation at 37° C.
+100 μL LA1 reagent
80 seconds incubation at 37° C.
1:50 dilution of the reaction mixture with OVB buffer.

Performance of the LA2 Test:

100 μL sample
240 seconds incubation at 37° C.
+100 μL LA2 reagent
80 seconds incubation at 37° C.
1:50 dilution of the reaction mixture with OVB buffer.

In each case 5 μL of the diluted reaction mixtures was used for determining the amount of F1+2 formed (see example 1).

A normal plasma sample without lupus anticoagulant (CPN), a sample with a high LA concentration (high LA control), and a sample with low LA concentration (low LA control) were tested, as were 1:1 dilutions of the high and low LA controls with normal plasma.

Figure 12:
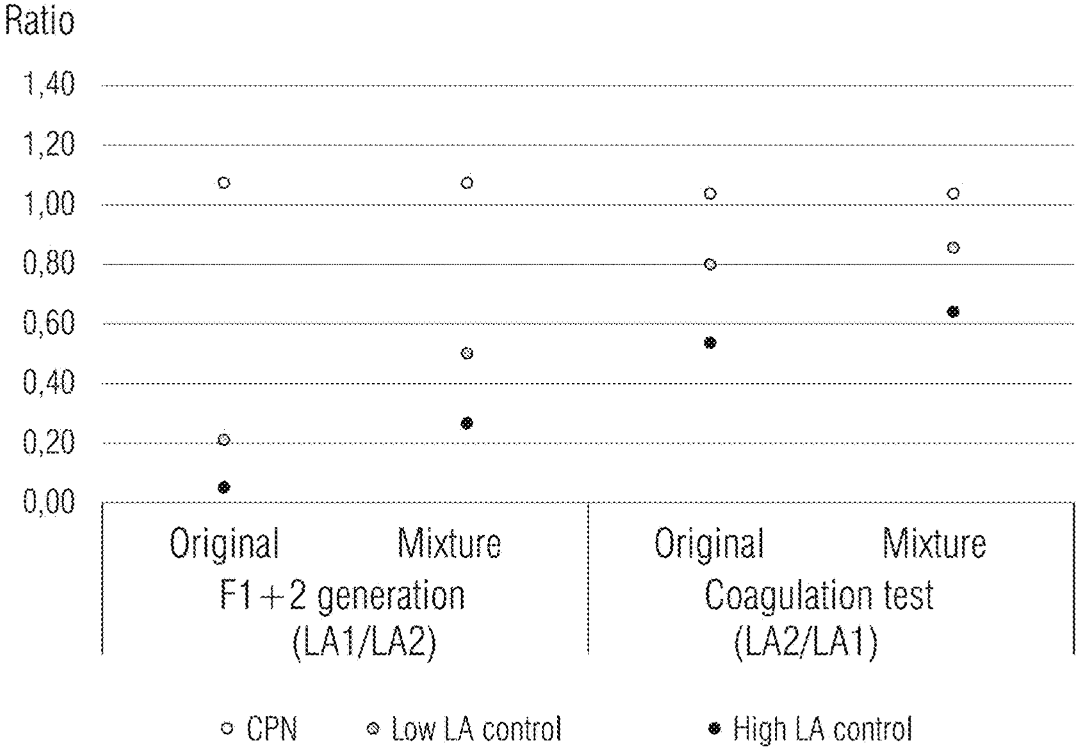
FIG. 12 shows a diagram in which a lupus anticoagulant coagulation test is compared with the lupus anticoagulant F1+2 generation test of an embodiment of the present invention. In the "original" test run, the sample is used as is, and in the "mixture" test run the sample is diluted 1:1 with a normal plasma.

FIG. 12 compares the LA2/LA1 ratios in the coagulation test with the LA1/LA2 ratios in the F1+2 generation test. For the normal plasma all ratios are close to 1. The sample with the low lupus anticoagulant content (low LA control) has a LA1/LA2 ratio in the F1+2 generation test (0.21) that is considerably lower than the LA2/LA1 ratio in the coagulation test (0.80). The F1+2 generation test thus responds considerably more sensitively to a weakly pathological lupus anticoagulant content than does the coagulation test.

In the lupus anticoagulant test the sample is diluted with normal plasma when factor deficiency is to be excluded as the cause for pathological values. In the 1:1 mixture with normal plasma (CPN), the ratio falls only to 0.86 in the coagulation test in the case of the low LA control, whereas in the F1+2 generation test the ratio still falls to 0.50. Even in a 1:1 mixture with normal plasma, this means that a weakly presenting lupus anticoagulant can be detected considerably more readily by measurement with the F1+2 generation.

Example 10: Establishment of an Anticoagulatory Blood Coagulation System Status by Determining the Strength of Anticoagulation of a Platelet Inhibitor In patients at increased risk of thrombosis, inhibition of platelets is indicated as prophylactic therapy. Such inhibition is accomplished in this example with prostaglandin E1, a substance that is known to inhibit platelet aggregation.

Whole blood from 3 normal and healthy blood donors was treated with 5% (v/v) of a prostaglandin E1 solution (end concentration in the sample 20 μmol/L) and incubated at room temperature for 20 minutes. This was followed by activation by collagen and further treatment and testing of the samples as described in example 7.

Figure 13:
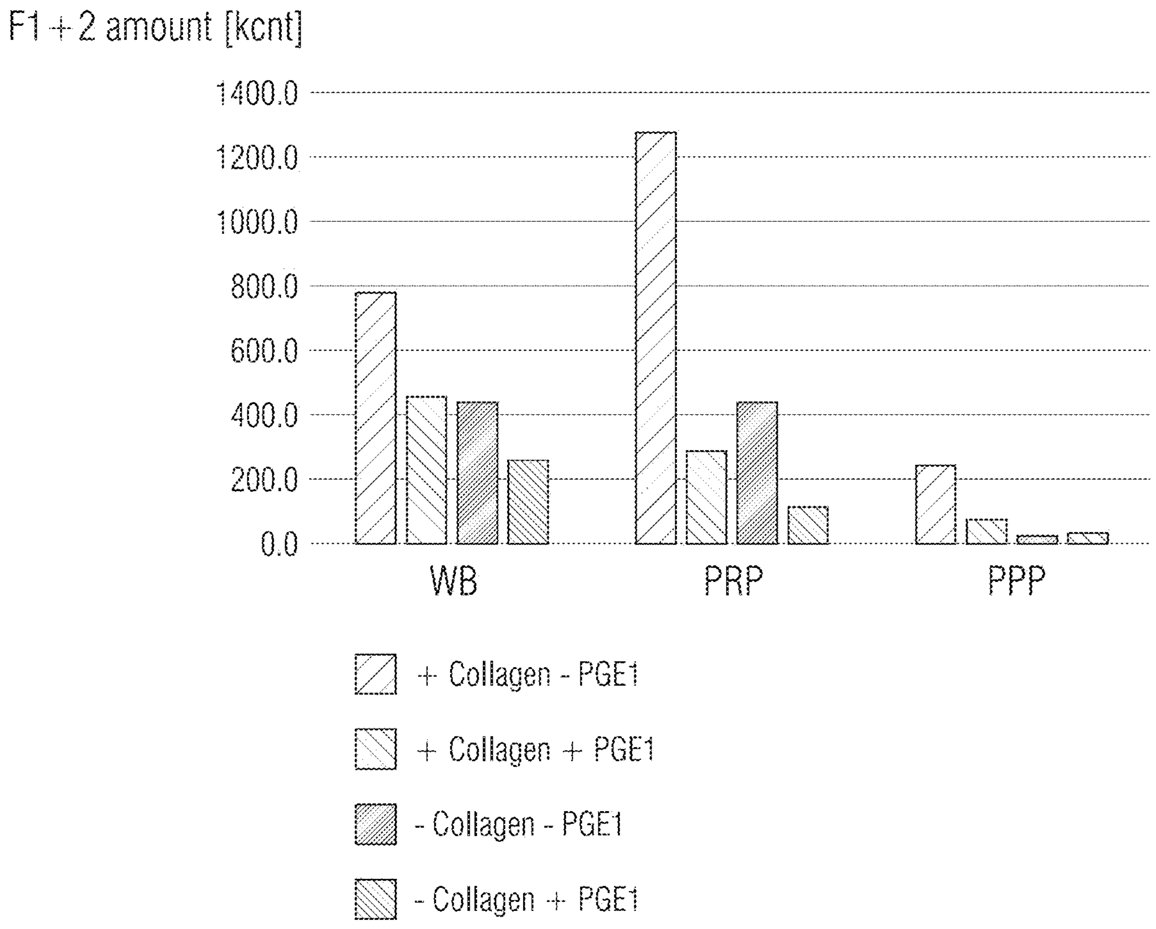
FIG. 13 shows a diagram depicting F1+2 generation determined according to an embodiment of the present invention (kcnt) in whole blood (WB), PRP, and PPP with/without inhibition of platelets by prostaglandin E1 (PGE1) and with/without subsequent activation of platelets by collagen.

FIG. 13 shows the F1+2 generation potentials of samples with and without PGE1 pretreatment and with and without subsequent collagen activation. The anticoagulatory effect of the platelet inhibitor PGE1 is seen both without and with activation of platelets by collagen, in the form of decreased F1+2 generation. The test of embodiments of the present invention can be used for the monitoring of treatment with platelet inhibitors.

Example 11: Highly Sensitive Determination of Factor VIII Activity

Three samples having a known factor VIII activity were prepared by mixing a normal plasma pool having a known factor VIII activity (control plasma N) with Owren's Veronal Buffer. These samples are mixed with reagents as follows. All reagents are marketed by Siemens Healthcare Diagnostics Products GmbH, Germany.

2 μL sample
+18 μL buffer
10 seconds incubation
+15 μL factor-VIII-deficient plasma (<1% factor VIII)
120 seconds incubation
+30 μL actin FS reagent (coagulation activator)
180 seconds incubation
+40 μL $CaCl_2$ solution
120 seconds incubation

+15 μL $H_2O$

As in example 1, 5 μL of the diluted reaction mixture was used for determining the amount of F1+2 formed in the reaction mixture.

After further incubation of the reaction run for a period of 6 minutes, the chemiluminescence signal in the arbitrary unit kilocounts (kcnt) was measured.

Results:

Sample 1 0% factor VIII=1876 kcnt

Sample 2 0.5% factor VIII=2469 kcnt

Sample 3 1.0% factor VIII=2779 kcnt

Sample 4 1.5% factor VIII=2901 kcnt

The F1+2 generation test permits a highly sensitive factor VIII activity test having large changes in signal in the range between 0 and 1.5% factor VIII activity.

The terminology used herein is for the purpose of describing particular example embodiments only and is not intended to be limiting. As used herein, the singular forms “a,” “an,” and “the” may be intended to include the plural forms as well, unless the context clearly indicates otherwise. The terms “comprises,” “comprising,” “including,” and “having,” are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term “comprising,” is to be understood as a non-restrictive term used to describe and claim various embodiments set forth herein, in certain aspects, the term may alternatively be understood to instead be a more limiting and restrictive term, such as “consisting of” or “consisting essentially of.” Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of “consisting of,” the alternative embodiment excludes any additional compositions, materials, components, elements, features, integers, operations, and/or process steps, while in the case of “consisting essentially of,” any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

In addition, disclosure of ranges includes disclosure of all values and further divided ranges within the entire range, including endpoints and sub-ranges given for the ranges. Thus ranges are, unless specified otherwise, inclusive of endpoints and include disclosure of all distinct values and further divided ranges within the entire range. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A method for establishing an individual’s blood coagulation system status, the method comprising:
- adding a coagulation activator to a sample from the individual to produce a reaction mixture;
- incubating the reaction mixture;
- quantitatively determining an amount of F1+2 in the reaction mixture; and
- comparing the amount of F1+2 in the reaction mixture with a reference value or reference value range that represents a normal blood coagulation system status of a healthy individual to establish the individual’s blood coagulation system status;
- wherein a procoagulatory status of the individual’s blood coagulation system is established when the amount of F1+2 quantitatively determined is above the reference value or reference value range that represents a normal blood coagulation system status of a healthy individual, or
- wherein an anticoagulatory status of the individual’s blood coagulation system is established when the amount of F1+2 quantitatively determined is below the reference value or reference value range that represents a normal blood coagulation system status of a healthy individual.

2. The method as claimed in claim 1, wherein the reaction mixture is diluted after the incubating the reaction mixture to produce a diluted reaction mixture, and the quantitative determination of the amount of F1+2 is carried out in the diluted reaction mixture.

3. The method as claimed in claim 2, wherein the quantitative determination of the amount of F1+2 in the reaction mixture or in the diluted reaction mixture is carried out using a F1+2-specific immunoassay.

4. The method as claimed in claim 3, wherein the F1+2-specific immunoassay comprises use of a first antibody having specificity for F1+2 and use of a second, F1+2-binding antibody or of a second antibody having specificity for the immune complex consisting of F1+2 and the first antibody.

5. The method as claimed in claim 4, wherein the first and second antibodies are each associated with a particulate solid phase and the quantitative determination of the amount of F1+2 comprises:
- mixing the reaction mixture with the particulate solid phases associated with the first and second antibodies; and
- measuring an agglutination of the particulate solid phases in the reaction mixture.

6. The method as claimed in claim 5, wherein the agglutination of the particulate solid phases in the reaction mixture is measured photometrically.

7. The method as claimed in claim 4, wherein the first antibody is associated with a first particulate solid phase and the second antibody is associated with a second particulate solid phase, and wherein the first particulate solid phase is associated with a first component of a signal-forming system and the second particulate solid phase is associated with a second component of a signal-forming system, and wherein the first and the second component of the signal-forming system interact with one another such that this produces a detectable signal when the first and the second component of the signal-forming system are brought into spatial proximity and an agglutination of the particulate solid phases in the reaction mixture is measured based on of the signal produced.

8. The method as claimed in claim 7, wherein the first component of the signal-forming system is a chemiluminescent agent and the second component of the signal-forming system is a photosensitizer or the first component of the signal-forming system is the photosensitizer and the second component of the signal-forming system is the chemiluminescent agent, and wherein a chemiluminescence in the reaction mixture is measured.

9. The method as claimed in claim 1, wherein the reaction mixture is incubated for a period of from 5 seconds to 60 minutes.

10. The method of claim 1, wherein the reaction mixture is incubated for a period of from 5 to 20 minutes.

11. The method as claimed in claim 1, wherein the coagulation activator is an activator of the plasmatic coagulation system.

12. The method as claimed in claim 11, wherein the activator of the plasmatic coagulation system is selected from the group consisting of thromboplastin, factor IIa, factor VIIa, factor IXa, factor Xa, factor XIa, factor XIIa, a snake venom, a negatively charged phospholipid, a calcium ion, a tissue factor, silica, kaolin, ellagic acid, diatomaceous earth, and a polyphosphate.

13. The method as claimed in claim 1, wherein the coagulation activator is a platelet activator.

14. The method as claimed in claim 13, wherein the platelet activator is selected from the group consisting of adenosine diphosphate (ADP), epinephrine, collagen, thrombin-receptor-activating peptide, thromboxane A2 mimic U46619, arachidonic acid, ristocetin, thrombin, von Willebrand factor, collagen-related peptide, convulxin, calcium ionophore A23187, and phorbol 12-myristate 13-acetate.

15. The method as claimed in claim 1, wherein the coagulation activator is a chemical or physical factor that heightens the procoagulatory effect of erythrocytes.

16. The method as claimed in claim 1, wherein the coagulation activator is a leukocyte-activating factor.

* * * * *